(12) United States Patent
Radhakrishnan et al.

(10) Patent No.: US 8,519,140 B2
(45) Date of Patent: Aug. 27, 2013

(54) METHOD FOR SYNTHESIZING PIRFENIDONE

(75) Inventors: Ramachandran Radhakrishnan, Fremont, CA (US); Michael Cyr, League City, TX (US); Sabine M. Pyles, Houston, TX (US)

(73) Assignee: Intermune, Inc., Brisbane, CA (US)

( * ) Notice: Subject to any disclaimer, the term of this patent is extended or adjusted under 35 U.S.C. 154(b) by 0 days.

(21) Appl. No.: 13/244,786

(22) Filed: Sep. 26, 2011

(65) Prior Publication Data

US 2012/0016133 A1  Jan. 19, 2012

Related U.S. Application Data

(63) Continuation of application No. 12/792,387, filed on Jun. 2, 2010, now abandoned.

(60) Provisional application No. 61/183,588, filed on Jun. 3, 2009.

(51) Int. Cl.
*A61K 31/44* (2006.01)
*C07D 211/72* (2006.01)

(52) U.S. Cl.
USPC .......................................... 546/290; 514/345

(58) Field of Classification Search
None
See application file for complete search history.

(56) References Cited

U.S. PATENT DOCUMENTS

| | | | |
|---|---|---|---|
| 3,839,346 A | 10/1974 | Sheekrishna et al. | |
| 5,356,898 A | 10/1994 | Belliotti et al. | |
| 2008/0319026 A1 | 12/2008 | Gant et al. | |
| 2009/0131485 A1 | 5/2009 | Liu et al. | |

FOREIGN PATENT DOCUMENTS

| | | |
|---|---|---|
| CN | 1386737 A | 12/2002 |
| CN | 1817862 A | 8/2006 |
| KR | 1020040022232 | 3/2004 |
| MX | A/2007/006349 | 2/2009 |
| WO | WO-02/085858 A1 | 10/2002 |
| WO | WO-03/014087 A1 | 2/2003 |
| WO | WO-2008/147170 A1 | 12/2008 |

OTHER PUBLICATIONS

Vogel, A., Practical Organic Chemistry, 3d ed., London, Longman Group, 1974, pp. 44-45 and 122-127.*
Hegde et al., "17. Pirfenidone (Idiopathic Pulmonary Fibrosis), Chapter 28 To Market, To Market—2008," *Ann Rep Med Chem*, vol. 44 (2009).
International Search Report from corresponding International Application No. PCT/US2010/037090, dated Mar. 1, 2011.
Ma et al., "Synthesis of pirfenidone," *Zhongguo Yiyao Gongye Zazhi*, 37(6):372-373 as summarized in Liu et al., "Synthetic Approaches to the 2008 New Drugs," *Mini-Reviews in Medicinal Chemistry*, 9:1655-75 (2009).
Zhang et al., Pirfenidone reduces fibronectin synthesis by cultured human retinal pigment epithelial cells, *Aust. N Z J Ophthalmol.*, 26 Suppl 1:S74-6 (1998).
Wu et al., Tissue distribution and plasma binding of a novel antifibrotics drug pifenidone in rats, Asian J. Pharmadynamics and Pharmacokinetics, 6(4):351-6 (2006).

* cited by examiner

*Primary Examiner* — Janet Andres
*Assistant Examiner* — Heidi Reese
(74) *Attorney, Agent, or Firm* — Marshall, Gerstein & Borun LLP; Carolyn Tang; John Bendrick

(57) ABSTRACT

A process for synthesizing pirfenidone from bromobenzene having less than about 0.15% by weight dibromobenze is disclosed. Also disclosed are processes of synthesizing pirfenidone without using ethyl acetate or n-butanol, and pirfenidone having controlled levels of ethyl acetate, n-butanol, di(5-methyl-2-pyridinone)benzenes, and other impurities having specified retention times. Also disclosed are formulated dosage forms including the disclosed pirfenidone.

18 Claims, No Drawings

METHOD FOR SYNTHESIZING PIRFENIDONE

CROSS REFERENCE TO RELATED APPLICATIONS

This is a continuation of U.S. patent application Ser. No. 12/792,387, filed Jun. 2, 2010, which in turn claims priority to U.S. Provisional Application No. 61/183,588, filed Jun. 3, 2009, the entire disclosures of which are each incorporated herein by reference.

BACKGROUND

1. Field of the Disclosure

This disclosure relates generally to methods for synthesizing pirfenidone. More specifically, this disclosure relates to a process for preparing pirfenidone using a bromobenzene reagent having less than about 0.15% by weight dibromobenzene and using copper(I) oxide as a catalyst, instead of a copper (I) or (II) halide.

2. Brief Description of the Related Art

Pirfenidone is a non-peptide synthetic molecule with a molecular weight of 185.23 daltons. Its chemical elements are expressed as $C_{12}H_{11}NO$, and its structure is known. The synthesis of pirfenidone has been worked out. Pirfenidone is manufactured and being evaluated clinically as a broad-spectrum anti-fibrotic drug. Pirfenidone has anti-fibrotic properties via: decreased TNF-α expression, decreased PDGF expression, and decreased collagen expression. Several pirfenidone Investigational New Drug Applications (INDs) are currently on file with the U.S. Food and Drug Administration. Phase II human investigations have been initiated or completed for pulmonary fibrosis, renal glomerulosclerosis, and liver cirrhosis. There have been other Phase II studies that used pirfenidone to treat benign prostate hypertrophy, hypertrophic scarring (keloids), and rheumatoid arthritis.

One important use of pirfenidone is known to be providing therapeutic benefits to patients suffering from fibrosis conditions such as Hermansky-Pudlak Syndrome (HPS) associated pulmonary fibrosis and idiopathic pulmonary fibrosis (IPF). Pirfenidone demonstrates a pharmacologic ability to prevent or remove excessive scar tissue found in fibrosis associated with injured tissues including that of lungs, skin, joints, kidneys, prostate glands, and livers. Published and unpublished basic and clinical research suggests that pirfenidone may safely slow or inhibit the progressive enlargement of fibrotic lesions, remove pre-existing fibrotic lesions, and prevent formation of new fibrotic lesions following tissue injuries.

It is understood that one mechanism by which pirfenidone exerts its therapeutic effects is by modulating cytokine actions. Pirfenidone is a potent inhibitor of fibrogenic cytokines and TNF-α. It is well documented that pirfenidone inhibits excessive biosynthesis or release of various fibrogenic cytokines such as TGF-β1, bFGF, PDGF, and EGF. Zhang S et al., *Australian New Eng. J. Ophthal.*, 26:S74-S76 (1998). Experimental reports also show that pirfenidone blocks the synthesis and release of excessive amounts of TNF-α from macrophages and other cells. Cain et al., *Int. J. Immunopharm.*, 20:685-695 (1998).

Pirfenidone has been studied in clinical trials for use in treatment of IPF. Thus, there is a need for a synthetic scheme that provides pirfenidone having sufficient purity as an active pharmaceutical ingredient (API) and involves efficient and economical processes. Prior batches of pirfenidone were shown to have residual solvent traces of ethyl acetate (e.g., about 2 ppm) and butanol.

SUMMARY

Disclosed herein are methods of preparing pirfenidone. More specifically, disclosed herein is a method of synthesizing pirfenidone comprising admixing bromobenzene, 5-methyl-2-pyridone, cuprous oxide, and an organic solvent under conditions sufficient to form pirfenidone, wherein the bromobenzene comprises less than about 0.15% by weight dibromobenzene. The admixing can be performed under elevated temperatures, for example at least about 100° C. The organic solvent can comprise dimethyl formamide.

In some embodiments, the method further comprises washing the pirfenidone with a saline solution. The saline solution can comprise about 10 wt % to about 15 wt % sodium chloride. In various embodiments, the method further comprises extracting the pirfenidone with an extracting solvent. The extracting solvent can comprise toluene.

In various embodiments, the method further comprises admixing a base with the bromobenzene, 5-methyl-2-pyridone, cuprous oxide, and organic solvent. The base can be an inorganic base. In a specific embodiment, the inorganic base comprises a carbonate, and more specifically, potassium carbonate.

In some embodiments, the method further comprises crystallizing the pirfenidone from a solvent mixture comprising heptanes and toluene to form purified pirfenidone. The method can also further comprise recrystallizing the purified pirfenidone by dissolving at least a portion of the purified pirfenidone in an acidic aqueous solution at an elevated temperature to form a pirfenidone solution; adding a basic solution to the pirfenidone solution until the pH is at least about 11; and cooling the basic pirfenidone solution to a temperature below about 20° C. to form recrystallized pirfenidone. In some cases, the elevated temperature is at least about 40° C. In various cases, the acidic aqueous solution comprises hydrochloric acid. In some cases, the basic solution comprises sodium hydroxide. In various cases, the basic pirfenidone solution is cooled to a temperature below about 10° C. In some cases, the purifying of the pirfenidone is performed in the absence of ethyl acetate and butanol. In a specific case, the pirfenidone prepared by the methods disclosed herein has a purity of at least 98% by weight or molar ratio and is essentially free of or free of ethyl acetate and butanol, where essentially free of describes a product where neither ethyl acetate nor butanol is intentionally added during the synthetic processes, as described herein. A pirfenidone composition essentially free of ethyl acetate and/or butanol can permit the presence of trace amounts of ethyl acetate and/or butanol which are carry-over impurities, e.g. present in the reagents or starting materials used in a synthetic process such as one described herein. The pirfenidone prepared can have a purity of at least 99%, and more preferably, at least 99.9% by weight or molar ratio.

In another aspect, disclosed herein is pirfenidone having less than about 0.1% by weight or molar ratio of a di(5-methyl-2-pyridone)benzene impurity, and preferably less than about 0.05% by weight or molar ratio of a di(5-methyl-2-pyridone)benzene impurity.

In yet another aspect, disclosed herein is pirfenidone having less than about 0.1% by weight or molar ratio of an impurity which elutes at a relative retention time of about 1.95 compared to the retention time of pirfenidone, when analyzed by liquid chromatography. Preferably, the pirfenidone has less than about 0.05% by weight or molar ratio of the impurity with the relative retention time of 1.95.

In still another aspect, disclosed herein is pirfenidone having less than about 0.1% by weight or molar ratio of an impurity which elutes at a relative retention time of about 1.24 compared to the retention time of pirfenidone, when analyzed by liquid chromatography. Preferably, the pirfenidone has less than about 0.05% by weight or molar ratio of the impurity with the relative retention time of 1.24.

In another aspect, pharmaceutical compositions comprising pirfenidone as disclosed herein and a pharmaceutically acceptable excipient are described.

DETAILED DESCRIPTION

Disclosed herein is an improved process for preparing pirfenidone. The process involves using a cuprous oxide catalyst to couple 5-methyl-2-pyridone and bromobenzene in an organic solvent. Without intending to be limited by any particular theory, it is believed that the purity of the bromobenzene is important, as amounts of a dibromobenzene impurity in the bromobenzene can lead to dimer-type byproducts, which can complicate the purification of the resulting pirfenidone. These dimer-type byproducts cannot be in a product intended as to be marketed as an active pharmaceutical ingredient (API), and they are difficult to remove from the intended pirfenidone product. Thus, the bromobenzene used in the disclosed processes preferably have an amount of dibromobenzene of less than about 0.15% by weight or molar ratio, and more preferably less than about 0.1% by weight or molar ratio or less than 0.05% by weight or molar ratio. The synthesis of pirfenidone is shown in Scheme 1, below.

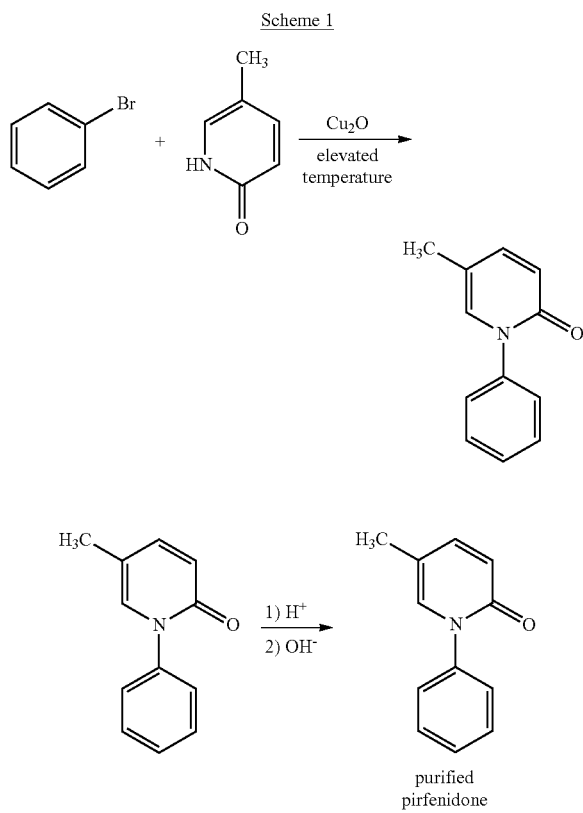

As used throughout this disclosure, impurities and purity of compounds are reported as a percentage (%). Unless indicated otherwise for specific cases, this percentage can be assessed based upon the weight of the sample or composition (e.g., a wt %), or based upon a molar ratio. Molar ratios (e.g., molar percentages) can be measured using these chromatographic techniques, such as high pressure/high performance liquid chromatography (HPLC), gas chromatography (GC), or capillary electrophoresis (CE). Molar ratios are molecular ratios of the specified compound to the total compounds present.

The bromobenzene preferably is pure monobromobenzene. The bromobenzene preferably is free of 1,4-dibromobenzene. The bromobenzene preferably is free of all dibromobenzenes (i.e., 1,2-dibromobenzene, 1,3-dibromobenzene, and 1,4-dibromobenzene). The bromobenzene preferably is free of tribromobenzenes (i.e., 1,2,3-tribromobenzene, 1,2,4-tribromobenzene, and 1,3,5-tribromobenzene). The bromobenzene preferably is free of tetrabromobenzenes (i.e., 1,2,3,4-tetrabromobenzene, 1,2,3,5-tetrachlorobenzene, and 1,2,4,5-tetrabromobenzene). The bromobenzene preferably is free of pentabromobenzene and hexabromobenzene.

The organic solvent of the coupling reaction can be any compatible organic solvent, such as an aprotic polar solvent. Non-limiting examples include tetrahydrofuran, diethyl ether, dimethyl formamide, dimethylsulfoxide, dichloromethane, dimethylsulfoxide, sulfolane, and mixtures thereof. In a specific preferred embodiment, the organic solvent comprises dimethyl formamide. Choice of the appropriate solvent can depend upon the temperature at which the reaction is run. A solvent having a boiling point above or around that of the reaction temperature is preferred.

The reaction can be performed at elevated temperatures. An elevated temperature is any temperature above room temperature (about 25° C.), and can be at least about 50° C., at least about 70° C., at least about 75° C., at least about 80° C., at least about 85° C., at least about 90° C., at least about 95° C., at least about 100° C., at least about 105° C., at least about 110° C., at least about 115° C., at least about 120° C., at least about 125° C., at least about at least about 130° C., or at least about 135° C., for example.

The reaction can be performed in the presence of a base. In some cases, the base can be an inorganic base. Inorganic bases include, but are not limited to, lithium hydroxide, potassium hydroxide, sodium hydroxide, sodium carbonate, potassium carbonate, sodium bicarbonate, potassium bicarbonate, and mixtures thereof. In one embodiment, the base comprises potassium carbonate.

Upon formation of the pirfenidone from the coupling reaction, the pirfenidone can optionally be washed with a saline solution. This washing step can remove salts used or formed during the coupling reaction. A saline solution can be a sodium chloride solution, for example a saturated brine solution. A high concentration sodium chloride solution provides low yield loss of pirfenidone in the aqueous layer, but a low concentration sodium chloride solution provides better compatibility with dimethyl formamide. Thus, an optimal sodium chloride solution concentration is high enough to minimize loss of pirfenidone in the aqueous layer, but low enough to allow a maximum amount of dimethyl formamide in the aqueous layer. Thus, in some embodiments, the sodium chloride solution is in a range of about 10 wt % to about 20 wt % sodium chloride, based on the weight of the solution.

The pirfenidone can additionally or alternatively be extracted with an organic solvent to remove impurities, such as residual organic solvent from the coupling reaction (e.g., dimethyl formamide). Examples of an extracting organic solvent include, but are not limited to, toluene, diethyl ether, tetrahydrofuran, methylene chloride, and mixtures thereof. In a specific embodiment, the pirfenidone is extracted with toluene. Extraction with toluene can allow for residual dimethyl formamide to remain in the aqueous layer.

The pirfenidone can be precipitated to form a more purified form of pirfenidone. Crude pirfenidone can be dissolved in a minimum amount of toluene and heptanes and heated to, e.g., about 50° C. to about 100° C. The solution is slowly cooled to about −5° C. to about 5° C. to allow precipitation of the pirfenidone. The resulting solid pirfenidone precipitate can be collected via filtration and dried.

The pirfenidone can additionally or alternatively be crystallized to form a more purified pirfenidone. For crystallization, the pirfenidone can be dissolved or partially dissolved in an acidic solution at an elevated temperature, such as at least about 35° C., at least about 40° C., or about 40° C. to about 50° C. The acidic solution can comprise any compatible inorganic or organic acid. The acidic solution preferably comprises an inorganic acid. Non-limiting examples of contemplated inorganic acids include sulfuric acid, hydrochloric acid, hydrobromic acid, nitric acid, phosphoric acid, and mixtures thereof. In a specific embodiment, the acidic solution comprises hydrochloric acid.

The resulting acidic pirfenidone solution can then be treated with addition of a basic solution until the pH of the pirfenidone solution is at least about 11. The basic solution can comprise any compatible inorganic or organic base. The basic solution is preferably an inorganic base. Non-limiting examples of contemplated inorganic bases include lithium hydroxide, potassium hydroxide, sodium hydroxide, sodium carbonate, potassium carbonate, sodium bicarbonate, potassium bicarbonate, and mixtures thereof. In a specific embodiment, the basic solution comprises sodium hydroxide.

The basic pirfenidone solution can then be cooled slowly to less than about 10° C., or about 0° C. to about 9° C. The resulting crystallized pirfenidone can then be collected via filtration and dried.

For pirfenidone used in clinical trials and as an API, it is important that the trace solvent levels be minimized, for example for regulatory requirements. Thus, in one aspect, the pirfenidone is essentially free of or free of ethyl acetate or butanol, for example from having been prepared without the use of ethyl acetate and/or butanol in any step. In some cases, the pirfenidone has less than about 30 ppm toluene, heptanes, or both, and preferably has less than about 20 ppm toluene, heptanes, or both. The prepared pirfenidone has a purity of at least 98% by weight or molar ratio, and can have a purity of preferably at least 99% by weight or molar ratio or at least 99.5% by weight or molar ratio or at least 99.6% by weight or molar ratio, at least 99.7% by weight or molar ratio, at least 99.8% by weight or molar ratio, or at least 99.9% by weight or molar ratio.

Pirfenidone according to the disclosure herein, for example prepared using a method disclosed herein, can additionally or alternatively have less than about 0.1% by weight or molar ratio, less than about 0.05% by weight or molar ratio, less than about 0.04% by weight or molar ratio, less than about 0.03% by weight or molar ratio, less than about 0.02% by weight or molar ratio, or less than about 0.01% by weight or molar ratio of a di(5-methyl-2-pyridinone)benzene impurity. Examples of such di(5-methyl-2-pyridinone)benzene impurities include one or more of

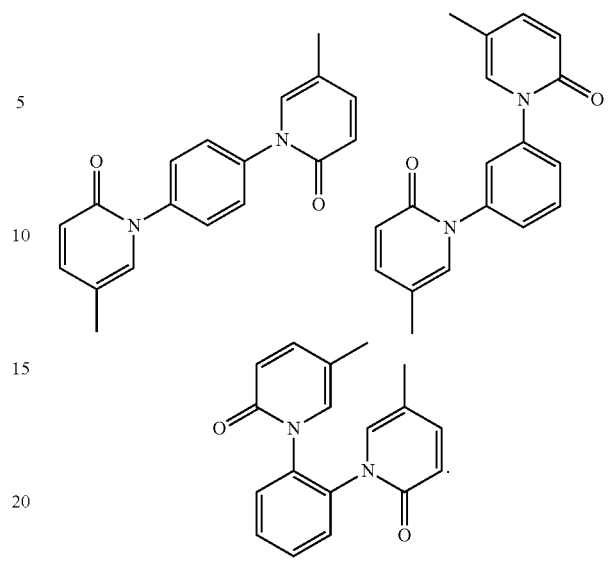

The pirfenidone can additionally or alternatively have less than about 0.1% by weight or molar ratio, less than about 0.05% by weight or molar ratio, less than about 0.04% by weight or molar ratio, less than about 0.03% by weight or molar ratio, less than about 0.02% by weight or molar ratio, or less than about 0.01% by weight or molar ratio of an impurity that has a relative retention time (RRT) of about 1.95 compared to the retention time of pirfenidone, when analyzed by liquid chromatography. The pirfenidone can additionally or alternatively have less than about 0.1% by weight or molar ratio, less than about 0.05% by weight or molar ratio, less than about 0.04% by weight or molar ratio, less than about 0.03% by weight or molar ratio, less than about 0.02% by weight or molar ratio, or less than about 0.01% by weight or molar ratio of an impurity that has a relative retention time (RRT) of about 1.24 compared to the retention time of pirfenidone, when analyzed by liquid chromatography.

An exemplary method for liquid chromatography (LC) analysis of pirfenidone is using a Hewlett-Packard 11000 Liquid Chromatograph, equipped with a UV detector operating at 220 nm and 310 nm, and a ZORBAX SB-Aq C-18, 5.0 μm, 250 mm×4.6 mm column. The mobile phases are Mobile Phase A (MPA) (200 μL phosphoric acid in 1000 mL water) and Mobile Phase B (MPB) (acetonitrile), which are pumped through the column at a flow rate of 1.0 mL/min and column temperature of 35° C. The mixture of MPA and MPB was a gradient profile over the course of the 25 minute run, as follows:

| Time (Minutes) | % MPA | % MPB |
| --- | --- | --- |
| 0 | 80 | 20 |
| 20 | 10 | 90 |
| 21 | 80 | 20 |
| 25 | 80 | 20 |

Pharmaceutical Compositions

While it is possible for the pirfenidone described herein to be administered alone, it may be preferable to formulate pirfenidone as pharmaceutical compositions. In particular, the pharmaceutical compositions can be useful for treating or preventing inflammatory conditions, e.g., conditions associated with p38 activity or cytokine activity or any combination thereof. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. A preferred subject is a mammal. A mammal includes any mammal, such as by way of non-limiting example, cattle, pigs, sheep, goats, horses, camels, buffalo, cats, dogs, rats, mice, and humans. A highly preferred subject mammal is a human.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may include a second active ingredient useful in the treatment or prevention of bacterial infection (e.g., a preservative, such as anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein may be formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed as a coating or as a matrix.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, pirfenidone described herein may be formulated for oral administration in a lipid-based formulation suitable for low solubility compounds. Lipid-based formulations can generally enhance the oral bioavailability of such compounds.

As such, a preferred pharmaceutical composition comprises a therapeutically or prophylactically effective amount of pirfenidone described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

A pharmaceutical composition contains a total amount of the active ingredient(s) sufficient to achieve an intended therapeutic effect when used with a suitable dosing regimen. More specifically, in some embodiments, the pharmaceutical composition contains a therapeutically effective amount. The total amounts of pirfenidone that may be combined with the carrier materials to produce a unitary dosing form will vary depending upon the host treated and the particular mode of administration. Preferably, the compositions are formulated in view of contemplated dosing regimens so that a dose of between 0.01 to 100 mg/kg body weight/day of pirfenidone is administered to a patient receiving the compositions. The total daily dose may be provided in divided daily doses (e.g. two times per day, three times per day, four times per day), and administered as multiple dosage forms containing sub-therapeutic dosage amounts (e.g., 267 mg per dosage form, administered as three dosage forms taken three times per day for a total of nine dosage forms administered, e.g. 2403 mg/day pirfenidone).

EXAMPLES

Coupling of Bromobenzene and 5-Methyl-2-pyridone

5-Methyl-2-pyridone (1.0 equivalents), potassium carbonate (1.2 equivalents), copper(I) oxide (0.05 equivalents), bromobenzene (1.8 equivalents, with a purity of at least 98%, preferably at least 99%, or at least 99.8%), and dimethyl formamide (2.0 volume equivalents) were charged into an inert reactor. This mixture was heated to 125° C. for about 18 hours. A sample was collected and analyzed for reaction completion. If reaction completion was not satisfactory, the reaction was maintained at 125° C. for an additional 2 hours. The reaction mixture was then cooled to 25° C. to form a slurry.

The resulting slurry was filtered in a Nutsche filter in order to remove salts. The filter cake was rinsed twice with toluene. The mother liquor and process liquor were collected in Vessel (A). A sodium chloride solution (15%) was charged into the product solution. The pH was adjusted to greater than or equal to 11.5 using a 32% sodium hydroxide solution. The mixture was then agitated. After agitation was stopped, the mixture was allowed to settle for at least 30 minutes to allow the two phases to separate. The organic layer was separated and the aqueous layer was extracted with toluene. The toluene extraction was added to the organic layer. The combined organics were then washed with a 15% sodium chloride solution and agitated for at least 15 minutes. The agitation was stopped and the layers were allowed to settle for at least 30 minutes. The organic layer was separated from the aqueous layer, and then carbon treated by flowing it through Zeta Carbon filters for 2 hours at 20-25° C. The carbon treated solution was then concentrated under vacuum to remove all water and much of the toluene.

Heptanes were then added to the concentrated solution, and it was heated to about 80° C. The solution was slowly cooled to about 0° C. over at least 7 hours. The pirfenidone precipitated out of the solution, was collected by filtration and dried, using a Nutsche filter/drier. The pirfenidone cake was washed twice with a mixture of toluene and heptanes (at 0° C.), then vacuum dried at a temperature of about 42° C. The crude pirfenidone was formed in about 85% yield.

Crystallization of Pirfenidone

Pirfenidone, a 32% hydrochloride solution, and deionized water were charged in an inert reactor. The mixture was heated to about 45° C., then a 32% sodium hydroxide solution was titrated into the mixture until the pH was at least 11. The temperature of the mixture was maintained at about 45° C. during the titration. Upon reaching the pH of at least 11, the mixture was then cooled slowly to 5° C., over the course of at least 2 hours. The pirfenidone crystallized from this cooled solution and was isolated in a Nutsche filter/drier. The pirfenidone cake was washed twice with deionized water (at 5° C.). The pirfenidone was then vacuum dried in the filter/drier at a temperature of about 45° C. The pirfenidone was also milled through a loop mill in order to reduce the particle size to less than 150 µm.

The resulting pirfenidone was then analyzed and the only residual solvents observed were toluene and heptanes at about 10 to 13 ppm. No ethyl acetate or butanol was detected in the pirfenidone. The amount of bis-conjugate in the purified pirfenidone was 0.03% or less. All impurities of the purified pirfenidone were less than about 0.05%.

The foregoing description is given for clearness of understanding only, and no unnecessary limitations should be understood therefrom, as modifications within the scope of the invention may be apparent to those having ordinary skill in the art.

Throughout the specification, where methods are described as including steps, components, or materials, it is contemplated that the compositions can also consist essentially of, or consist of, any combination of the recited steps, components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed:

1. A method of synthesizing pirfenidone comprising
admixing bromobenzene, 5-methyl-2-pyridone, cuprous oxide, and an organic solvent under conditions sufficient to form pirfenidone,
wherein the bromobenzene comprises less than about 0.15% by weight or molar ratio dibromobenzene, and
wherein the pirfenidone has a purity of at least 99% by weight or molar ratio and no impurity greater than 0.05% by weight or molar ratio.

2. The method of claim 1, further comprising washing the pirfenidone with a saline solution.

3. The method of claim 1, further comprising extracting the pirfenidone from the organic solvent mixture with an extracting organic solvent.

4. The method of claim 3, wherein the extracting organic solvent comprises toluene.

5. The method of claim 1, further comprising admixing a base with the bromobenzene, 5-methyl-2-pyridone, cuprous oxide, and organic solvent.

6. The method of claim 5, wherein the base comprises a carbonate.

7. The method of claim 6, wherein the carbonate comprises potassium carbonate.

8. The method of claim 1, wherein the organic solvent comprises dimethyl formamide.

9. The method of claim 1, further comprising crystallizing the pirfenidone from a solvent mixture comprising heptanes and toluene to form purified pirfenidone.

10. The method of claim 9, further comprising recrystallizing the purified pirfenidone by
dissolving at least a portion of the purified pirfenidone in an acidic aqueous solution at an elevated temperature to form a pirfenidone solution;
adding a base to the pirfenidone solution until the pH is at least about 11 to form a basic pirfenidone solution; and
cooling the basic pirfenidone solution to a temperature below about 20° C. to form recrystallized pirfenidone.

11. The method of claim 9, comprising performing the crystallizing in the absence of ethyl acetate and in the absence of butanol.

12. The method of claim 11, further comprising milling the pirfenidone to a particle size of less than 150 µm.

13. The method of claim 1, wherein the bromobenzene comprises less than about 0.1% by weight or molar ratio dibromobenzene.

14. The method of claim 1, wherein the bromobenzene comprises less than about 0.05% by weight or molar ratio dibromobenzene.

15. The method of claim 1, further comprising formulating the pirfenidone into a pharmaceutical composition by combining it with a pharmaceutically acceptable excipient.

16. The method of claim 15, wherein the pharmaceutical composition is in the form of a solid, liquid solution, emulsion, suspension, powder, syrup, elixir, cream, ointment, tablet, capsule, troche, lozenge, or granule.

17. The method of claim 15, wherein the pharmaceutical composition is suitable for oral administration.

18. The method of claim 16, wherein the pharmaceutical composition is in the form of a granule, capsule or tablet.

* * * * *